US012676317B2

(12) United States Patent
Yu

(10) Patent No.: US 12,676,317 B2
(45) Date of Patent: Jul. 7, 2026

(54) OVER-DISCHARGE PROTECTION FOR ELECTROCHEMICAL CELLS

(71) Applicant: Medtronic, Inc., Minneapolis, MN (US)

(72) Inventor: Lu Yu, Shakopee, MN (US)

(73) Assignee: Medtronic, Inc., Minneapolis, MN (US)

( * ) Notice: Subject to any disclaimer, the term of this patent is extended or adjusted under 35 U.S.C. 154(b) by 757 days.

(21) Appl. No.: 17/969,928

(22) Filed: Oct. 20, 2022

(65) Prior Publication Data

US 2024/0136536 A1     Apr. 25, 2024
US 2024/0234742 A9     Jul. 11, 2024

(51) Int. Cl.
    *H01M 4/66*         (2006.01)
    *A61N 1/378*        (2006.01)
              (Continued)

(52) U.S. Cl.
    CPC ............ *H01M 4/667* (2013.01); *A61N 1/378* (2013.01); *A61N 1/3956* (2013.01);
              (Continued)

(58) Field of Classification Search
    CPC ...... H01M 4/667; H01M 4/661; H01M 4/662; H01M 10/4235; H01M 10/44;
              (Continued)

(56) References Cited

U.S. PATENT DOCUMENTS 6,596,439 B1    7/2003    Tsukamoto et al.
9,583,779 B2    2/2017    Chiang et al.
             (Continued)

FOREIGN PATENT DOCUMENTS

CN     109802121       5/2019
CN     109802121 A   *   5/2019
             (Continued)

OTHER PUBLICATIONS

PCT Search Report and Written Opinion for PCT/IB2023/059513 dated Nov. 23, 2023 (12 pages).
             (Continued)

*Primary Examiner* — Daniel S Gatewood
(74) *Attorney, Agent, or Firm* — Mueting Raasch Group

(57) ABSTRACT

Electrochemical cells and methods of providing over-discharge protection of the same are disclosed. An electrochemical cell may include a cathode, an anode, a separator, and an electrolyte. The cathode may include a cathode current collector and a cathode active material disposed on at least a portion of the cathode current collector. The anode may include an anode current collector and an anode active material disposed on at least a portion of the anode current collector. The anode current collector may include an anode conductive material and a lithophilic metal layer disposed on the anode conductive material. The lithophilic metal layer may define an outer surface of the anode current collector. The separator may be arranged between the anode and the cathode to prevent direct contact between the anode and the cathode. The electrolyte may transport ions between the cathode and the anode.

20 Claims, 3 Drawing Sheets

(51) Int. Cl.

| | |
|---|---|
| *A61N 1/39* | (2006.01) |
| *H01M 4/02* | (2006.01) |
| *H01M 10/42* | (2006.01) |
| *H01M 10/44* | (2006.01) |

(52) U.S. Cl.
CPC ........... *H01M 4/661* (2013.01); *H01M 4/662* (2013.01); *H01M 10/4235* (2013.01); *H01M 10/44* (2013.01); *H01M 2004/027* (2013.01)

(58) Field of Classification Search
CPC ....... H01M 2004/027; H01M 2220/30; H01M 10/052; H01M 10/0525; A61N 1/378; A61N 1/3956; A61N 1/362; A61N 1/37512; A61N 1/3975; Y02E 60/10
See application file for complete search history.

(56) References Cited

U.S. PATENT DOCUMENTS

| | | | | |
|---|---|---|---|---|
| 2021/0210791 A1* | 7/2021 | Suzuki | .................. | H01M 4/587 |
| 2022/0158167 A1 | 5/2022 | Xiao | | |
| 2023/0039594 A1 | 2/2023 | Lee | | |
| 2024/0113305 A1* | 4/2024 | Shin | ........................ | C23C 28/04 |

FOREIGN PATENT DOCUMENTS

| | | | | |
|---|---|---|---|---|
| CN | 110061191 | 9/2021 | | |
| CN | 114846645 | 8/2022 | | |
| EP | 3312911 | 4/2018 | | |
| JP | 5165843 | 3/2013 | | |
| WO | WO 2022/173085 | 8/2022 | | |
| WO | WO-2022173085 A1 * | 8/2022 | ........... | C23C 28/322 |

OTHER PUBLICATIONS

Chen Xiao-Ru et al., "Role of Lithiophilic Metal Sites in Lithium Metal Anodes", Energy & Fuels, vol. 35, No. 15, Aug. 5, 2021.

Li Dongdong et al., "Au-Coated Carbon Fabric as Janus Current Collector for Dendrite-Free Flexible Lithium Metal Anode and Battery," Applied Physics Reviews, American Institute of Physics, 2 Huntington Quadrangle, Melville, NY 11747, vol. 9, No. 1, Mar. 23, 2022.

Qian Yi et al., "Constructing Ultrafine Lithiophilic Layer on MXene Paper by Sputtering for Stable and Flexible 3D Lithium Metal Anode," Chemical Engineering Journal, Elsevier, Amsterdam, NL, vol. 421, Apr. 8, 2021.

* cited by examiner

200

202

Over-discharge an
electrochemical cell

204

Prevent dissolution of the
anode current collector

OVER-DISCHARGE PROTECTION FOR ELECTROCHEMICAL CELLS

FIELD

The present disclosure relates to, among other things, batteries or electrochemical cells.

TECHNICAL BACKGROUND

Batteries or electrochemical cells are generally used to provide power to devices when wired connections to external power sources may be undesirable or inconvenient. For example, batteries may be used in portable devices such as laptops and mobile phones or in implantable medical devices where constant connection to external power sources may be cumbersome or excessively restrictive. Lithium-ion and lithium metal batteries or electrochemical cells can experience irreversible damage when the electrochemical cells are over-discharged. Over-discharge may drive the anode potential that is typically negative relative to the cathode to be positive relative to the cathode. Such change in polarity due to over-discharge can cause dissolution of the anode current collector into electrolyte of the electrochemical cell. The resultant dissolved ions can be re-deposited on internal cell components and possibly induce an internal short. Re-deposition of the anode current collector material onto the cathode and the anode can also block the intercalation/deintercalation of lithium ions resulting in degraded electrochemical cell performance. In some cases, the dissolution of the anode current collector can also cause anode delamination, loss of active materials, and open circuit conditions.

BRIEF SUMMARY

The present disclosure describes, among other things, batteries or electrochemical cells with a built-in over-discharge protection using anode current collectors that include a lithophilic metal layer. A lithophilic metal layer that defines an outer surface of an anode current collector can prevent the dissolution of the anode current collector when electrochemical cells are over-discharged. Accordingly, the batteries and electrochemical cells described herein can be over-discharged without irreversibly damaging such electrochemical cells. Additionally, the lithophilic metal layer may increase conductivity of the anode current collector without significantly increasing the cost of electrochemical cells relative to electrochemical cells that do not include a lithophilic metal layer.

Described herein, among other things, is an electrochemical cell comprising a cathode, an anode, a separator, and an electrolyte. The cathode may comprise a cathode current collector and a cathode active material disposed on at least a portion of the cathode current collector. The anode may comprise an anode current collector and an anode active material disposed on at least a portion of the anode current collector. The anode current collector may comprise an anode conductive material and a lithophilic metal layer disposed on the anode conductive material. The lithophilic metal layer may define an outer surface of the anode current collector. The separator may be arranged between the anode and the cathode to prevent direct contact between the anode and the cathode. The electrolyte may transport ions between the cathode and the anode.

In general, in one aspect, the present disclosure describes an implantable medical device comprising a housing, one or more electrical components disposed in the housing, and one or more electrochemical cells electrically coupled to at least one electrical component of the one or more electrical components. Each of the one or more electrochemical cells may comprise a cathode, an anode, a separator, and an electrolyte. The cathode may comprise a cathode current collector and a cathode active material disposed on at least a portion of the cathode current collector. The anode may comprise an anode current collector and an anode active material disposed on at least a portion of the anode current collector. The anode current collector may comprise an anode conductive material and a lithophilic metal layer disposed on the anode conductive material. The lithophilic metal layer may define an outer surface of the anode current collector. The separator may be arranged between the anode and the cathode to prevent direct contact between the anode and the cathode. The electrolyte may transport ions between the cathode and the anode.

In general, in one aspect, the present disclosure describes a method providing over-discharge protection of an electrochemical cell. The electrochemical cell may comprise a cathode, an anode, a separator, and an electrolyte. The cathode may comprise a cathode current collector and a cathode active material disposed on at least a portion of the cathode current collector. The anode may comprise an anode current collector and an anode active material disposed on at least a portion of the anode current collector. The anode current collector may comprise an anode conductive material and a lithophilic metal layer disposed on the anode conductive material. The lithophilic metal layer may define an outer surface of the anode current collector. The separator may be arranged between the anode and the cathode to prevent direct contact between the anode and the cathode. The electrolyte may transport ions between the cathode and the anode. The method may comprise over-discharging the electrochemical cell and preventing dissolution of the anode current collector into the electrolyte using the lithophilic metal layer.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

BRIEF DESCRIPTION OF THE DRAWINGS

The following detailed description of specific embodiments of the present disclosure can be best understood when read in conjunction with the following drawings, in which.

The schematic drawing is not necessarily to scale.

DETAILED DESCRIPTION

Reference will now be made in greater detail to various embodiments of the subject matter of the present disclosure, one or more embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

Lithium-ion and lithium metal batteries or electrochemical cells may experience irreversible damage when the electrochemical cells are over-discharged. Over-discharge may drive the electric potential of the anode to be positive relative to the cathode. Such a change in polarity due to over-discharge can cause dissolution of typical anode current collectors into the electrolyte of the electrochemical cell. Typical anode current collectors of electrochemical cells may include copper or other materials susceptible to dissolution when electrochemical cells are over-discharged. The resultant dissolved ions (e.g., cupric ions) can be re-deposited on internal cell components and possibly induce an internal short. Additionally, the anode current collector material can be re-deposited onto cathode and anode active materials that can impede the transfer of lithium ions between the cathode and the anode (e.g., intercalation/deintercalation) resulting in degraded electrochemical cell performance. In some cases, the dissolution of the anode current collector can also cause anode delamination, loss of active materials, and open circuit conditions.

To prevent damage or degraded performance of the electrochemical cell caused by over-discharge, outer surfaces of anode current collectors may be formed or defined by a lithophilic metal layer. As used herein, the term "lithophilic metal" may refer to materials or alloys that aid in desirable lithium nucleation and are not subject to dissolution caused by typical electrochemical cell over-discharge conditions. Lithophilic metals may include, for example, silver, gold, platinum, indium, palladium, etc. Additionally, the use of a lithophilic metal layer in anode current collectors as described herein may improve desirable lithium nucleation and the cycling performance of lithium-ion or lithium metal rechargeable batteries.

Figure 1:
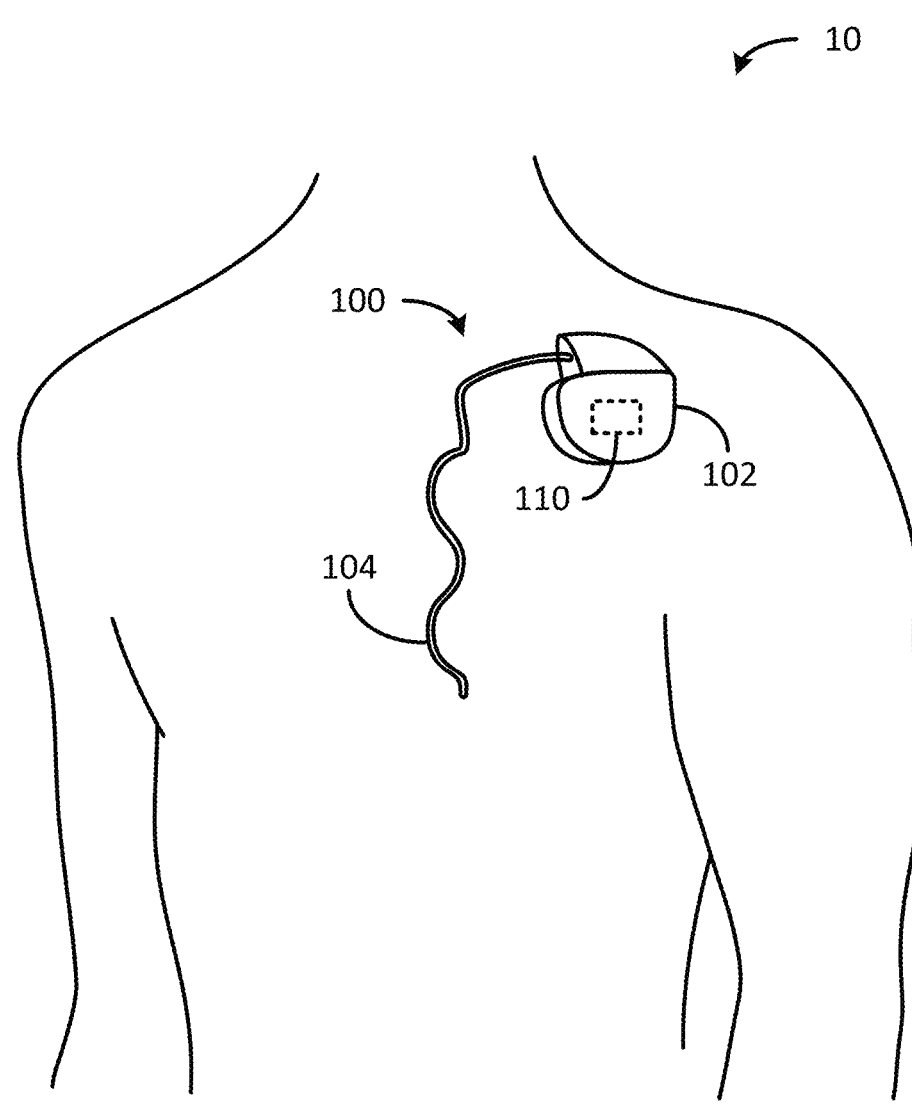
FIG. 1 is a conceptual drawing illustrating an embodiment of a battery used in an implantable medical device.

An embodiment of a device or system that includes a battery or electrochemical cell that includes an anode current collector as described herein, is depicted in FIG. 1. FIG. 1 shows a conceptual drawing illustrating a device or system 100 in conjunction with a patient 10. As depicted in FIG. 1, the device 100 includes a housing 102 that defines the exterior of an implantable medical device. The device 100 may be or may be included in, any suitable implantable medical device such as, for example, implantable pulse generators, implantable cardioverter defibrillators, implantable cardiac contractility modulators, implantable neurostimulators, implantable mechanical assist devices, etc.

The device 100 may also include one or more leads 104 to deliver therapeutic electrical pulses to desired treatment areas of the patient 10. The leads 104 may include one or more electrodes (not shown) to facilitate delivery of the therapeutic electrical pulses to the desired treatment areas. In one or more embodiments, the device 100 may include one or more electrodes without any leads. For example, when the device 100 can be implanted at the desired treatment area, leads may not be needed to deliver the therapeutic electrical pulses.

The device 100 may include one or more electrical components disposed in the housing 102. The one or more electrical components may include one or more pulse generators, switches, passive electrical components (e.g., capacitors, inductors, or resistors), digital logic circuits, controllers, processors, or other components to facilitate operation of the device 100. Additionally, the device 100 may include one or more electrochemical cells 110 electrically coupled to at least one electrical component of the one or more electrical components. In other words, the one or more electrochemical cells may be configured to provide power to the at least one electrical component.

Figure 2:
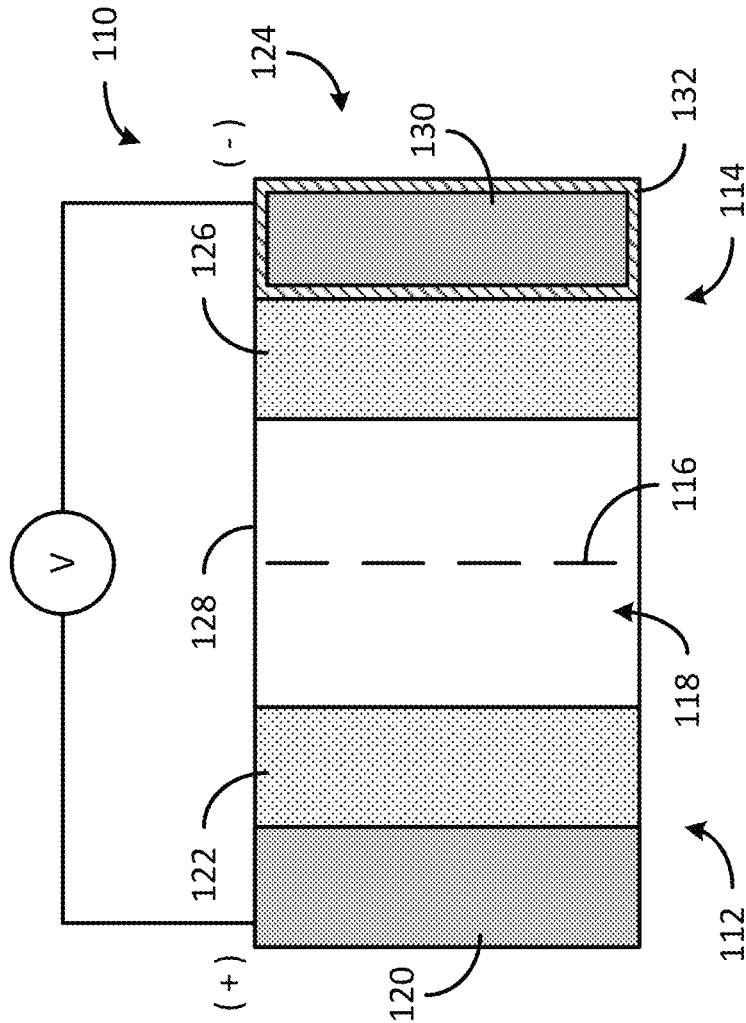
FIG. 2 is a schematic diagram of an embodiment of an electrochemical cell.

A schematic representation of an embodiment of an electrochemical cell 110 is depicted in FIG. 2. The electrochemical cell 110 may be, or may form a single cell of, a lithium battery. The electrochemical cell 110 may be any suitable lithium electrochemical cell. For example, the electrochemical cell 110 may be a lithium-ion electrochemical cell, a lithium metal electrochemical cell, or other lithium electrochemical cell. Accordingly, the batteries described herein may be, for example, lithium-ion batteries, lithium metal batteries, or other lithium batteries. Additionally, the electrochemical cell 110 may be a primary cell (e.g., non-rechargeable) or a secondary cell (e.g., rechargeable).

The electrochemical cell 110 may include a cathode 112, an anode 114, a separator 116, and an electrolyte 118. The electrochemical cell 110 may also include a cell housing 128 that defines the exterior of the electrochemical cell 110. In other words, each of the cathode 112, the anode 114, the separator 116, and the electrolyte 118 may be disposed in the cell housing 128. The cathode 112 and the anode 114 may be provided as relatively flat or planar plates, wrapped or wound in a spiral or other configuration (e.g., an oval configuration), or as a folded configuration. The separator 116 (e.g., a polymeric microporous separator) may be arranged between the anode 114 and the cathode 112 to prevent direct contact between the anode 114 and the cathode 112.

The cathode 112 may include a cathode current collector 120 and a cathode active material 122 disposed on at least a portion of the cathode current collector 120. The cathode current collector 120 may include any one or more materials such as, for example, aluminum, titanium, etc. The cathode active material 122 may include any one or more materials such as, for example, lithium-metal oxides (e.g., $LiCoO_2$, $LiMn_2O_4$, $Li(Ni_xMn_yCo_z)O_2$, $Li(Ni_xCo_yAl_z)O_2$, etc.), vanadium oxides, olivines (e.g., $LiFePO_4$), rechargeable lithium oxides, etc. In general, the cathode 112 may be disposed in the cell housing 128. However, the cathode current collector 120 may be partially disposed outside of the cell housing 128 or a portion of the cathode current collector 120 may be electrically coupled to at least a portion of the cell housing 128.

The anode 114 may include an anode current collector 124 and an anode active material 126 disposed on at least a portion of the anode current collector 124. The anode current collector 124 may include an anode conductive material 130 and a lithophilic metal layer 132 disposed on the anode conductive material 130. The anode conductive material 130 may include any one or more conductive materials such as, for example, copper, gold, aluminum, or other conductive material.

The lithophilic metal layer 132 may define an outer surface of the anode current collector 124. In other words, the lithophilic metal layer 132 may cover the anode conductive material 130 such that the electrolyte 118 is prevented from coming into contact with the anode conductive material 130. Accordingly, the lithophilic metal layer 132 may prevent dissolution of the anode conductive material 130 because the anode conductive material 130 is not in contact with the electrolyte 118 and, therefore, cannot be dissolved in the electrolyte 118. The lithophilic metal layer 132 may have a thickness of at least 5 nanometers and no greater than 100 nanometers. The lithophilic metal layer 132 may include any one or more lithophilic metals such as, for example, silver, gold, platinum, indium, palladium, etc. In general, the lithophilic metal layer 132 may be substantially free of any materials or impurities in addition to the lithophilic metal or metals.

The anode active material 126 may include lithium. The anode active material 126 may be substantially free of any additional materials or impurities. Alternatively, the anode active material 126 may also include one or more additional materials such as, for example, magnesium, silver, zinc, aluminum, tin, and silicon.

During charging and discharging of the electrochemical cell 110, lithium ions may move between the cathode 112 and the anode 114. Such movement of lithium ions between the cathode 112 and the anode 114 may be referred to as ion transfer. For example, when the electrochemical cell 110 is discharged, lithium ions flow from the anode 114 to the cathode 112. In contrast, when the electrochemical cell 110 is charged, lithium ions flow from the cathode 112 to the anode 114. While the separator 116 may prevent direct contact between the cathode 112 and the anode 114, the separator may permit the flow of ions between the anode 114 and the cathode 112. Furthermore, the electrolyte 118 may facilitate transport of ions between the anode 114 and the cathode 112.

The electrolyte 118 may be disposed in the cell housing 128. The electrolyte 118 may generally fill at least a portion of any space inside the cell housing 128 that is not filled by the other components (e.g., the cathode 112, the anode 114, the separator 116, insulators, conductors, etc.) of the electrochemical cell 110. The electrolyte 118 may have an electrical potential. When the cathode 112 and the anode 114 are electrically isolated from the cell housing 128, the cell housing 128 may float at the electrical potential of the electrolyte. The electrolyte 118 may be one or more of, for example, a liquid, a gel, a paste, etc. The material composition of the electrolyte may depend on a cell type of the electrochemical cell 110. The electrolyte 118 may include, for example, lithium salt, sulfuric acid, fluorinated sulfone, or other suitable electrolyte.

Figure 3:
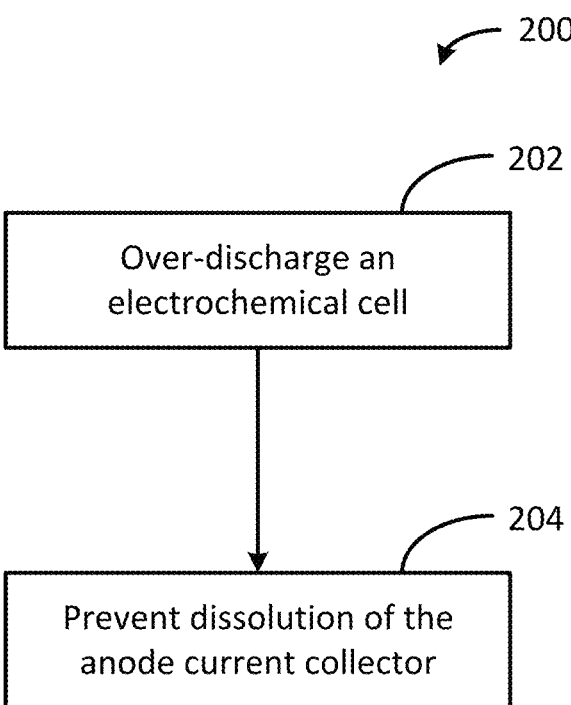
FIG. 3 is flow diagram of an embodiment of a method or process for preventing overheating of an electrochemical cell.

A method or process 200 for providing over-discharge protection of an electrochemical cell (e.g., electrochemical cell 110 of FIGS. 1 and 2) is depicted in FIG. 3. The method 200 may include over-discharging the electrochemical cell 202. To over-discharge the electrochemical cell, electrical energy may be provided to electrical components of a device or system (e.g., device 100 of FIG. 1) by the electrochemical cell beyond its nominal capacity. Accordingly, over-discharge of the electrochemical cell may result in the anode having a greater electrical potential than the cathode.

The method 200 may include preventing dissolution of the anode current collector into the electrolyte using the lithophilic metal layer 204. The lithophilic metal layer may prevent the electrolyte from coming into contact with the anode conductive material. Additionally, the lithophilic metal layer may not be subject to dissolution in the electrolyte under typical over-discharge conditions. Accordingly, the anode conductive material may not be dissolved into the electrolyte because the lithophilic metal layer provides a barrier between the anode conductive material the electrolyte.

The invention is defined in the claims. However, below there is provided a non-exhaustive list of non-limiting examples. Any one or more of the features of these examples may be combined with any one or more features of another example, embodiment, or aspect described herein.

Example Ex1: An electrochemical cell comprising: a cathode comprising: a cathode current collector; and a cathode active material disposed on at least a portion of the cathode current collector; an anode comprising: an anode current collector comprising: an anode conductive material; and a lithophilic metal layer disposed on the anode conductive material, the lithophilic metal layer defining an outer surface of the anode current collector; an anode active material disposed on at least a portion of the anode current collector; and a separator arranged between the anode and the cathode to prevent direct contact between the anode and the cathode; and an electrolyte to transport ions between the cathode and the anode.

Example Ex2: The electrochemical cell as in claim Ex1, wherein the lithophilic metal layer defines all outer surfaces of the anode current collector that are in direct contact with the electrolyte.

Example Ex3: The electrochemical cell as in claim Ex1, wherein the lithophilic metal layer comprises at least one of silver or gold.

Example Ex4: The electrochemical cell as in claim Ex1, wherein the lithophilic metal layer comprises a silver alloy or a gold alloy.

Example Ex5: The electrochemical cell as in claim Ex1, wherein the lithophilic metal layer consists essentially of silver.

Example Ex6: The electrochemical cell as in claim Ex1, wherein the lithophilic metal layer consists of silver.

Example Ex7: The electrochemical cell as in claim Ex1, wherein the lithophilic metal layer has a thickness of at least 5 nanometers and no greater than 100 nanometers.

Example Ex8: The electrochemical cell as in claim Ex1, wherein the anode active material comprises copper.

Example Ex9: The electrochemical cell as in claim Ex1, further comprising a cell housing and wherein the cathode active material, the anode active material, the separator, and the electrolyte are disposed within the cell housing.

Example Ex10: An implantable medical device comprising: a housing; one or more electrical components disposed in the housing; and one or more electrochemical cells electrically coupled to at least one electrical component of the one or more electrical components, each of the one or more electrochemical cells comprising: a cathode comprising: a cathode current collector; and a cathode active material disposed on at least a portion of the cathode current collector;

an anode comprising: an anode current collector comprising: an anode conductive material; and a lithophilic metal layer disposed on the anode conductive material, the lithophilic metal layer defining an outer surface of the anode current collector; an anode active material disposed on at least a portion of the anode current collector; and a separator arranged between the anode and the cathode to prevent direct contact between the anode and the cathode; and an electrolyte to transport ions between the cathode and the anode.

Example Ex11: The implantable medical device as in claim Ex10, wherein the implantable medical device comprises an implantable cardioverter defibrillator.

Example Ex12: The device as in claim Ex10, wherein the lithophilic metal layer defines all outer surfaces of the anode current collector that are in direct contact with the electrolyte.

Example Ex13: The device as in claim Ex10, wherein the lithophilic metal layer comprises at least one of silver or gold.

Example Ex14: The device as in claim Ex10, wherein the lithophilic metal layer comprises a silver alloy or a gold alloy.

Example Ex15: The device as in claim Ex10, wherein the lithophilic metal layer consists essentially of silver.

Example Ex16: The device as in claim Ex10, wherein the lithophilic metal layer consists of silver.

Example Ex17: The device as in claim Ex10, wherein the lithophilic metal layer has a thickness of at least 5 nanometers and no greater than 100 nanometers.

Example Ex18: The device as in claim Ex10, wherein the anode active material comprises copper.

Example Ex19: The device as in claim Ex10, further comprising a cell housing and wherein the cathode active material, the anode active material, the separator, and the electrolyte are disposed within the cell housing.

Example Ex20: A method for providing over-discharge protection of an electrochemical cell, the electrochemical cell comprising: a cathode comprising: a cathode current collector; and a cathode active material disposed on at least a portion of the cathode current collector;

an anode comprising: an anode current collector comprising: an anode conductive material; and a lithophilic metal layer disposed on the anode conductive material, the lithophilic metal layer defining an outer surface of the anode current collector; an anode active material disposed on at least a portion of the anode current collector; and a separator arranged between the anode and the cathode to prevent direct contact between the anode and the cathode; and an electrolyte to transport ions between the cathode and the anode; and the method comprising: over-discharging the electrochemical cell; and preventing dissolution of the anode current collector into the electrolyte using the lithophilic metal layer.

Example Ex21: The method as in claim Ex20, wherein the lithophilic metal layer defines all outer surfaces of the anode current collector that are in direct contact with the electrolyte.

Example Ex22: The method as in claim Ex20, wherein the lithophilic metal layer comprises at least one of silver or gold.

Example Ex23: The method as in claim Ex20, wherein the lithophilic metal layer comprises a silver alloy or a gold alloy.

Example Ex24: The method as in claim Ex20, wherein the lithophilic metal layer consists essentially of silver.

Example Ex25: The method as in claim Ex20, wherein the lithophilic metal layer consists of silver.

Example Ex26: The method as in claim Ex20, wherein the lithophilic metal layer has a thickness of at least 5 nanometers and no greater than 100 nanometers.

Example Ex27: The method as in claim Ex20, wherein the anode active material comprises copper.

Example Ex28: The method as in claim Ex20, further comprising a cell housing and wherein the cathode active material, the anode active material, the separator, and the electrolyte are disposed within the cell housing.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising." For example, a microfluidic device comprising a sheet having an interconnected microporous structure, a double-sided adhesive layer, and a film may consist of, or consist essentially of, the sheet, the adhesive layer and the film.

As used herein, "consisting essentially of", as it relates to a compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods.

The term "substantially" as used here has the same meaning as "significantly," and can be understood to modify the term that follows by at least about 90 percent, at least about 95 percent, or at least about 98 percent. The term "substantially free" of a particular compound means that the compositions of the present invention contain less than 1,000 parts per million (ppm) of the recited compound.

As used herein, the term "not substantially" has the same meaning as "not significantly," and can be understood to have the inverse meaning of "substantially," i.e., modifying the term that follows by not more than 25 percent, not more than 10 percent, not more than 5 percent, or not more than 2 percent.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An electrochemical cell comprising:
a cathode comprising:
   a cathode current collector; and
   a cathode active material disposed on at least a portion of the cathode current collector;
an anode comprising:
   an anode current collector comprising:
      an anode conductive material; and
      a lithiophilic metal layer disposed on the anode conductive material, the lithiophilic metal layer defining all outer surfaces of the anode current collector;
   an anode active material disposed on at least a portion of the anode current collector; and
a separator arranged between the anode and the cathode to prevent direct contact between the anode and the cathode; and
an electrolyte to transport ions between the cathode and the anode, wherein the lithiophilic metal layer is in direct contact with the electrolyte and is configured to prevent dissolution of the anode current collector into the electrolyte.

2. The electrochemical cell as in claim 1, wherein the lithiophilic metal layer defines all outer surfaces of the anode current collector that are in direct contact with the electrolyte.

3. The electrochemical cell as in claim 1, wherein the lithiophilic metal layer comprises at least one of silver or gold.

4. The electrochemical cell as in claim 1, wherein the lithiophilic metal layer comprises a silver alloy or a gold alloy.

5. The electrochemical cell as in claim 1, wherein the lithiophilic metal layer consists essentially of silver.

6. The electrochemical cell as in claim 1, wherein the lithiophilic metal layer consists of silver.

7. The electrochemical cell as in claim 1, wherein the lithiophilic metal layer has a thickness of at least 5 nanometers and no greater than 100 nanometers.

8. An implantable medical device comprising:
a housing;
one or more electrical components disposed in the housing; and
one or more electrochemical cells electrically coupled to at least one electrical component of the one or more electrical components, each of the one or more electrochemical cells comprising:
   a cathode comprising:
      a cathode current collector; and
      a cathode active material disposed on at least a portion of the cathode current collector;
   an anode comprising:
      an anode current collector comprising:
         an anode conductive material; and
         a lithiophilic metal layer disposed on the anode conductive material, the lithiophilic metal layer defining all outer surfaces of the anode current collector;
      an anode active material disposed on at least a portion of the anode current collector; and

10 a separator arranged between the anode and the cathode to prevent direct contact between the anode and the cathode; and
an electrolyte to transport ions between the cathode and the anode, wherein the lithiophilic metal layer is in direct contact with the electrolyte and is configured to prevent dissolution of the anode current collector into the electrolyte.

9. The implantable medical device as in claim 8, wherein the implantable medical device comprises an implantable cardioverter defibrillator.

10. The device as in claim 8, wherein the lithiophilic metal layer comprises at least one of silver or gold.

11. The device as in claim 8, wherein the lithiophilic metal layer comprises a silver alloy or a gold alloy.

12. The device as in claim 8, wherein the lithiophilic metal layer consists essentially of silver.

13. The device as in claim 8, wherein the lithiophilic metal layer consists of silver.

14. The device as in claim 8, wherein the lithiophilic metal layer has a thickness of at least 5 nanometers and no greater than 100 nanometers.

15. A method for providing over-discharge protection of an electrochemical cell, the electrochemical cell comprising:
a cathode comprising:
   a cathode current collector; and
   a cathode active material disposed on at least a portion of the cathode current collector;
an anode comprising:
   an anode current collector comprising:
      an anode conductive material; and
      a lithiophilic metal layer disposed on the anode conductive material, the lithiophilic metal layer defining all outer surfaces of the anode current collector;
   an anode active material disposed on at least a portion of the anode current collector; and
a separator arranged between the anode and the cathode to prevent direct contact between the anode and the cathode; and
an electrolyte to transport ions between the cathode and the anode, wherein the lithiophilic metal layer is in direct contact with the electrolyte and is configured to prevent dissolution of the anode current collector into the electrolyte; and
the method comprising:
   over-discharging the electrochemical cell; and
   preventing dissolution of the anode current collector into the electrolyte using the lithiophilic metal layer.

16. The method as in claim 15, wherein the lithiophilic metal layer defines all outer surfaces of the anode current collector that are in direct contact with the electrolyte.

17. The method as in claim 15, wherein the lithiophilic metal layer comprises at least one of silver or gold.

18. The method as in claim 15, wherein the lithiophilic metal layer comprises a silver alloy or a gold alloy.

19. The method as in claim 15, wherein the lithiophilic metal layer consists essentially of silver.

20. The method as in claim 15, wherein the lithiophilic metal layer consists of silver.

* * * * *